(12) United States Patent
Sugiura

(10) Patent No.: US 9,629,569 B2
(45) Date of Patent: Apr. 25, 2017

(54) MAGNETIC RESONANCE IMAGING APPARATUS AND IMAGE GENERATION METHOD FOR GUIDANCE AND POSITIONING

(75) Inventor: Satoshi Sugiura, Otawara (JP)

(73) Assignee: TOSHIBA MEDICAL SYSTEMS CORPORATION, Otawara-shi (JP)

( * ) Notice: Subject to any disclaimer, the term of this patent is extended or adjusted under 35 U.S.C. 154(b) by 250 days.

(21) Appl. No.: 12/425,740

(22) Filed: Apr. 17, 2009

(65) Prior Publication Data

US 2009/0264731 A1    Oct. 22, 2009

(30) Foreign Application Priority Data

Apr. 17, 2008  (JP) .................... 2008-108011

(51) Int. Cl.
| | |
|---|---|
| A61B 5/055 | (2006.01) |
| A61B 6/00 | (2006.01) |
| G01R 33/56 | (2006.01) |
| G01R 33/561 | (2006.01) |
| G01R 33/563 | (2006.01) |
| A61B 5/00 | (2006.01) |
| G01R 33/54 | (2006.01) |

(52) U.S. Cl.
CPC ............ *A61B 5/055* (2013.01); *A61B 5/0037* (2013.01); *A61B 6/488* (2013.01); *G01R 33/5601* (2013.01); *G01R 33/5613* (2013.01); *G01R 33/5635* (2013.01); *A61B 5/7285* (2013.01); *A61B 6/541* (2013.01); *G01R 33/543* (2013.01); *G01R 33/5605* (2013.01)

(58) Field of Classification Search
CPC  G01R 33/5601; G01R 33/5635; A61B 5/055; A61B 5/0037

USPC ........ 324/309, 314, 318, 321; 600/407, 410, 600/411, 413, 419, 420, 422
See application file for complete search history.

(56) References Cited

U.S. PATENT DOCUMENTS

| | | | | |
|---|---|---|---|---|
| 5,513,854 | A | * | 5/1996 | Daver .......................... 700/91 |
| 5,565,777 | A | * | 10/1996 | Kanayama et al. .......... 324/309 |
| 5,771,893 | A | * | 6/1998 | Kassai et al. ................ 600/419 |
| 6,002,254 | A | * | 12/1999 | Kassai et al. ................ 324/306 |

(Continued)

FOREIGN PATENT DOCUMENTS

| | | |
|---|---|---|
| JP | 9-117447 | 5/1997 |
| JP | 10-192252 | 7/1998 |

(Continued)

OTHER PUBLICATIONS

English full translation of JP H09-117447, Jun. 5, 1997.*

(Continued)

*Primary Examiner* — Serkan Akar
(74) *Attorney, Agent, or Firm* — Nixon & Vanderhye P.C.

(57) ABSTRACT

A medical imaging apparatus includes a positioning image acquisition unit which acquires a positioning image concerning a subject, a unit which sets an region of interest in the positioning image in accordance with specification performed by an operator, a monitoring image acquisition unit which repeatedly acquires a monitoring image concerning the subject at predetermined time intervals, and a generation unit which combines an region-of-interest image representing the region of interest with the monitoring image to generate a display image every time the monitoring image is acquired.

17 Claims, 4 Drawing Sheets

(56) References Cited

U.S. PATENT DOCUMENTS

| | | | |
|---|---|---|---|
| 6,320,377 B1* | 11/2001 | Miyazaki et al. | 324/306 |
| 6,498,486 B1* | 12/2002 | Ookawa | 324/312 |
| 6,510,335 B1* | 1/2003 | Miyazaki | 600/419 |
| 6,603,992 B1* | 8/2003 | Debbins et al. | 600/420 |
| 6,781,375 B2* | 8/2004 | Miyazaki et al. | 324/314 |
| 6,782,286 B2* | 8/2004 | Miyazaki | 600/410 |
| 6,801,800 B2* | 10/2004 | Miyazaki et al. | 600/410 |
| 6,946,836 B2* | 9/2005 | Kuhara | 324/307 |
| 7,190,164 B2* | 3/2007 | Kuhara | 324/309 |
| 7,254,437 B2* | 8/2007 | Miyazaki | 600/410 |
| 7,308,298 B2* | 12/2007 | Miyazaki | 600/410 |
| 7,336,076 B2* | 2/2008 | Kuhara | 324/318 |
| 7,423,428 B2* | 9/2008 | Kuhara | 324/318 |
| 7,570,050 B2* | 8/2009 | Sugiura | 324/307 |
| 7,587,232 B2* | 9/2009 | Sugiura | 600/410 |
| 7,647,086 B2* | 1/2010 | Miyazaki et al. | 600/419 |
| 2002/0021128 A1* | 2/2002 | Kuhara | 324/309 |
| 2002/0032376 A1* | 3/2002 | Miyazaki et al. | 600/410 |
| 2002/0169372 A1* | 11/2002 | Miyazaki | 600/410 |
| 2002/0188190 A1* | 12/2002 | Kassai et al. | 600/410 |
| 2003/0042905 A1* | 3/2003 | Miyazaki et al. | 324/314 |
| 2003/0158476 A1* | 8/2003 | Takabayashi et al. | 600/420 |
| 2003/0171671 A1* | 9/2003 | Miyazaki | 600/420 |
| 2004/0047497 A1* | 3/2004 | Daw | G06T 19/00 382/128 |
| 2004/0059213 A1* | 3/2004 | Kassai et al. | 600/410 |
| 2004/0068175 A1* | 4/2004 | Miyazaki et al. | 600/410 |
| 2005/0206379 A1* | 9/2005 | Kojima | 324/309 |
| 2005/0248344 A1* | 11/2005 | Kuhara | 324/309 |
| 2006/0100503 A1* | 5/2006 | Takai et al. | 600/422 |
| 2007/0066886 A1* | 3/2007 | Kuhara et al. | 600/413 |
| 2007/0145978 A1* | 6/2007 | Kuhara | 324/318 |
| 2007/0203412 A1* | 8/2007 | Sugiura | 600/410 |
| 2007/0247159 A1* | 10/2007 | Kuhara | 324/321 |
| 2007/0265522 A1* | 11/2007 | Kassai et al. | 600/411 |
| 2008/0009708 A1* | 1/2008 | Machida | 600/414 |
| 2008/0071166 A1* | 3/2008 | Miyazaki | 600/419 |
| 2008/0081987 A1* | 4/2008 | Miyazaki | 600/410 |
| 2009/0245607 A1* | 10/2009 | Sugiura | 382/131 |
| 2009/0253984 A1* | 10/2009 | Yui et al. | 600/420 |
| 2009/0264731 A1* | 10/2009 | Sugiura | 600/419 |

FOREIGN PATENT DOCUMENTS

| | | |
|---|---|---|
| JP | 2000-511789 | 9/2000 |
| JP | 2001-61809 | 3/2001 |
| JP | 2002-253524 | 9/2002 |
| JP | 2003-235827 | 8/2003 |
| JP | 2004-57237 | 2/2004 |
| JP | 2006-198225 | 8/2006 |

OTHER PUBLICATIONS

Foo et al., "Automated Detection of Bolus Arrival and Initiation of Data Acquisition in Fast, Three-dimensional, Gadolinium-enhanced MR Angiography", *Technical Developments and Instrumentation—Radiology*, 1997, vol. 203, pp. 275-280.

Wilman et al., "Fluoroscopically Triggered Contrast-enhanced Three-dimensional MR Angiography with Elliptical Centric View Order: Application to Renal Arteries", *Radiology*, 1997, vol. 205, pp. 137-146.

Office Action (3 pgs.) dated Mar. 6, 2013 issued in corresponding Japanese Application No. 2008-108011 with an at least partial English-language translation thereof (3 pgs.).

Office Action (3 pgs.) dated Sep. 24, 2013 issued in corresponding Japanese Application No. 2008-108011 with an at least partial English-language translation thereof (3 pgs.).

Office Action (3 pgs.) dated Mar. 24, 2015 issued in corresponding Japanese Application No. 2014-144518.

\* cited by examiner

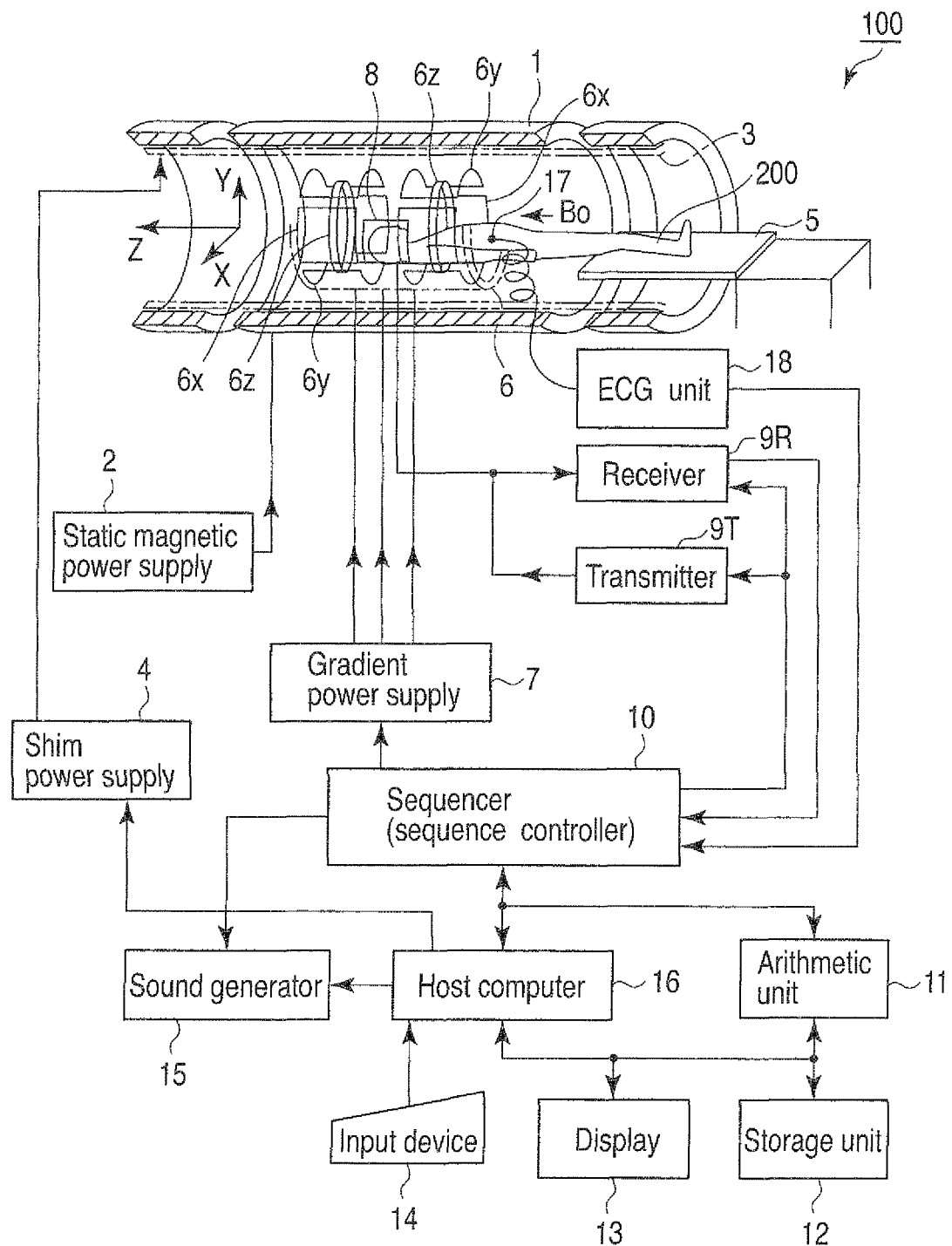
F I G. 1

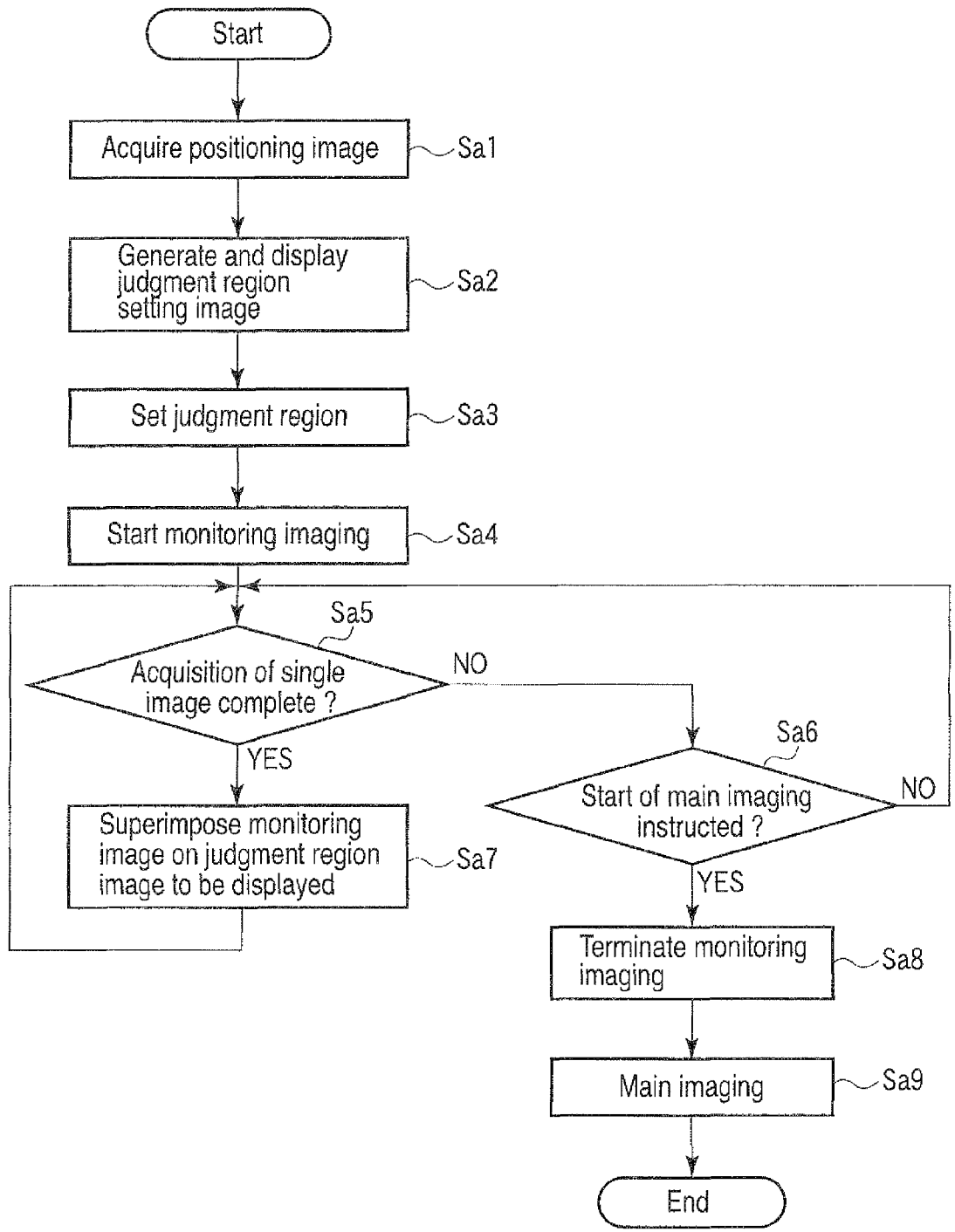
F I G. 2

MAGNETIC RESONANCE IMAGING APPARATUS AND IMAGE GENERATION METHOD FOR GUIDANCE AND POSITIONING

CROSS-REFERENCE TO RELATED APPLICATIONS

This application is based upon and claims the benefit of priority from prior Japanese Patent Application No. 2008-108011, filed Apr. 17, 2008, the entire contents of which are incorporated herein by reference.

BACKGROUND OF THE INVENTION

1. Field of the Invention

The present invention relates to an apparatus and method for repeatedly acquiring a monitoring image that is used to monitor a change in a given region of interest of a subject.

2. Description of the Related Art

As one of the fields of application of the magnetic resonance imaging (MRI) method, there is magnetic resonance angiography (MRA). MRA can be realized by MRI through the use of various fundamental contrast generation principles such as the time-of-flight (TOF) effect or phase shift effect. One extensively used method (which will be referred to as contrast MRA hereinafter) is to rapidly inject a contrast medium having a longitudinal relaxation time (T1) reduction effect into the human body and imaging blood having this contrast medium mixed therein. Using contrast MRA makes it possible to obtain images of a main artery, a renal artery, or a blood vascular system including a neck region, a head region, a foot region, and others.

Imaging time in contrast MRA is generally in the range of approximately several seconds to several tens of seconds. Therefore, only one imaging operation may be performed per contrast medium injection operation.

However, the contrast medium is usually injected at a point distant from the region considered an imaging target (which will be referred to as the target region hereinafter). Therefore, the time at which the contrast medium reaches the target region to enable acquisition of an image having good contrast lags the contrast medium injection time. Further, the delay is dependent on, for example, the cardiac rate, blood pressure, or blood flow rate of the subject, and hence it is not fixed.

Under the circumstances, in contrast MRA, appropriately setting imaging timing is important, and ingenuity in realizing this setting has been conventionally exercised as follows.

For example, firstly, there is known a technology that continuously acquires a magnetic resonance signal from a limited monitoring region (for example, the inside of a main artery on the upstream side of a target region) close to the target region prior to the contrast MRA imaging, presents an operator with a change in signal intensity with time, and starts imaging in synchronization with a timing at which the signal intensity is increased to a threshold value or above (see PCT National Publication No. 2000-511789).

A second technology is suggested as an alternative of the first technology, and this technology adopts fluoroscopy using a two-dimensional imaging method to monitor a relatively wide range and directly provides a state of movement of a contrast medium as a change in image signal (see Radiology, Vol. 205, p. 137 [1997]).

In this second technology, since a wide range can be continuously imaged, how the contrast medium flows in a subject can be displayed in real time. That is, for example, how the contrast medium injected from an upper arm or a subject flows through a lung, an atrium, and a main artery can be displayed in real time. An operator chooses a proper timing at which the contrast medium reaches a target region based on this display and instructs starting the contrast MRA imaging. The contrast MRA imaging is started at a timing that the contrast medium reaches an object region determined on an upstream side of the target region.

Thirdly, there is known a technology that performs subtraction processing with respect to an image signal obtained in a second conventional example or maximum value projection processing of multi-slice data in order to further clearly display how a contrast medium moves (see JP-A 2003-235827 [KOKAI]).

It should be noted that setting a region of interest (ROI) required to measure a signal value on a two-dimensional image is known (see JP-A H10-192252 [KOKAI]), but specification of the position of this ROI by an operator is not performed before the contrast medium reaches a target region.

However, in the first technology, an increase in signal intensity is not sufficiently ascertained in some cases as described in Radiology, Vol. 203, p. 275 (1997). It is considered that this increase cannot be ascertained because a blood flow signal cannot be satisfactorily observed due to breathing or body movements in a monitoring region. Further, with this first technology, a monitoring region having a small volume must be appropriately positioned, and there is the inconvenience that operation is complicated.

On the other hand, with the second and third technologies, it is hard for an operator lacking sufficient experience in contrast MRA inspections to accurately ascertain that the contrast medium has reached a target region, and it is possible that the contrast MRA imaging is not started at the right time. This is because, in a fluoroscopy image, the signal is weak at positions except where the contrast medium has entered, and hence the position of a target region or an object region is hard to ascertain.

BRIEF SUMMARY OF THE INVENTION

Under the circumstances, making it possible for an inexperienced operator to accurately judge the time for starting contrast MRA imaging has been demanded.

According to a first aspect of the present invention, there is provided a medical imaging apparatus comprising: a positioning image acquisition unit which acquires a positioning image concerning a subject; a unit which sets a region of interest in the positioning image in accordance with specification performed by an operator; a monitoring image acquisition unit which repeatedly acquires a monitoring image concerning the subject at predetermined time intervals; and a generation unit which combines a region-of-interest image representing the region of interest with the monitoring image to generate a display image every time the monitoring image is acquired.

According to a second aspect of the present invention, there is provided a medical display image generation method comprising: acquiring a positioning image concerning a subject; setting a region of interest in the positioning image in accordance with specification made by an operator; repeatedly acquiring a monitoring image concerning the subject at predetermined time intervals; combining a region-of-interest image showing the region of interest with the monitoring image to display a display image every time the monitoring image is acquired.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1 is a view showing an outline structure of a magnetic resonance imaging apparatus according to an embodiment of the present invention;

FIG. 2 is a flowchart showing a processing procedure for contrast MRA imaging using a host computer depicted in FIG. 1;

DETAILED DESCRIPTION OF THE INVENTION

Figure 3:
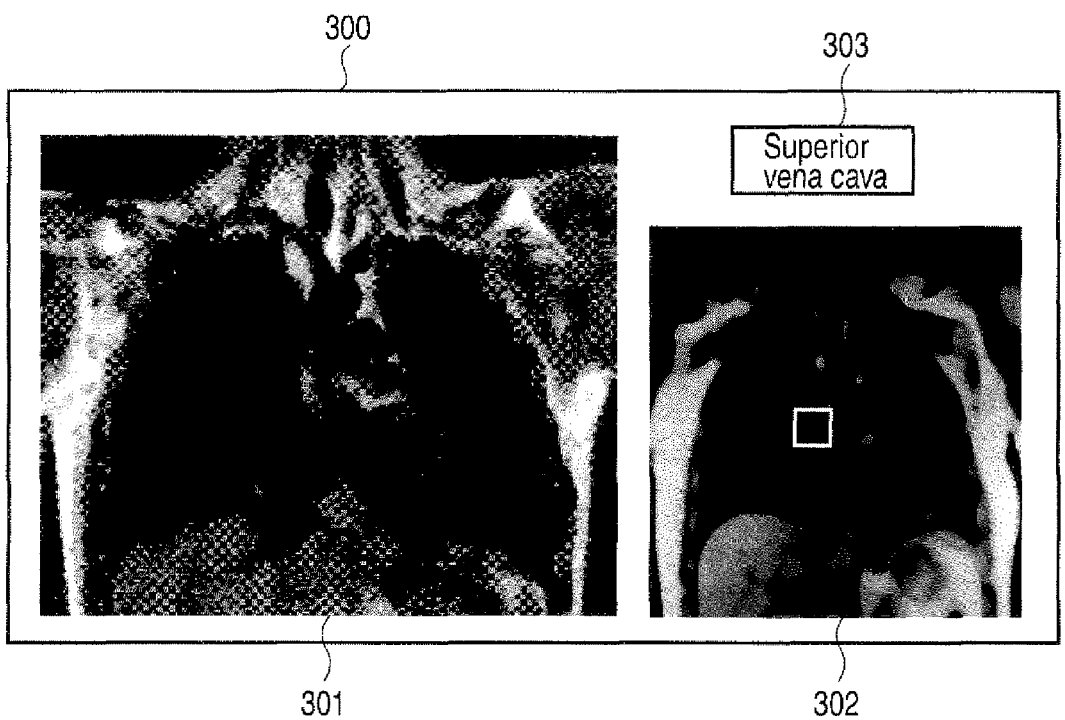
FIG. 3 is a view showing an example of a judgment region setting image.

By taking a magnetic resonance imaging (MRI) apparatus as an example of one type of medical imaging apparatus, an embodiment of the present invention will be described with reference to the accompanying drawings.

FIG. 1 is a diagram showing the configuration of the MRI apparatus according to the embodiments of this invention.

The MRI apparatus 100 comprises a bed unit, a static-magnetic-field generating unit, a gradient-magnetic-field generating unit, a receiving/transmitting unit, and a control/operating unit. The MRI apparatus 100 has, as components of these units, a magnet 1, a static magnetic power supply 2, a shim coil 3, a shim power supply 4, a top plate 5, a gradient coil unit 6, a gradient power supply 7, an RF coil unit 8, a transmitter 9T, a receiver 9R, a sequencer (sequence controller) 10, an arithmetic unit 11, a storage unit 12, a display 13, an input device 14, an audio unit 15, and a host computer 16. To the MRI apparatus 100, an electrocardiograph unit is connected and detects an ECG signal representing the cardiac phase of the subject 200.

The static-magnetic-field generating unit includes the magnet 1 and the static magnetic power supply 2. The magnet 1 is, for example, a superconducting magnet or a normal magnet. The static magnetic power supply 2 supplies a current to the magnet 1. The static-magnetic-field generating unit therefore generates a static magnetic field B0 in a cylindrical aperture (examination space) into which the subject 200 is moved. The direction of the static magnetic field B0 virtually coincides with the axis (i.e., the Z-axis) of the examination space. The static-magnetic-field generating unit further includes the shim coil 3. The shim coil 3 generates a correction magnetic field for rendering the static magnetic field uniform when a current is supplied to it from the shim power supply 4 under the control of the host computer 16.

The bed unit moves the top plate 5, on which the subject 200 is lying, into or out of the examination space.

The gradient-magnetic-field generating unit includes the gradient coil unit 6 and the gradient power supply 7. The gradient coil unit 6 is arranged in the magnet 1. The gradient coil unit 6 has three coils 6x, 6y and 6z that can generate three gradient magnetic fields extending in mutually orthogonal X-, Y- and Z-axes, respectively. The gradient power supply 7 supplies pulse currents to the coils Ex, 6y and 6z, under the control of the sequencer 10. Supplied with the pulse current, the coils 6x, 6y and 6z generate gradient magnetic fields. The gradient-magnetic-field generating unit controls the pulse currents supplied from the gradient power supply 7 to the coils 6x, 6y and 6z. Thus, the gradient-magnetic-field generating unit synthesizes gradient magnetic fields extending in the three physical axes (i.e., the X-, Y- and Z-axes), respectively. The unit sets these magnetic fields in logical axes defined by a slice gradient magnetic field Gs, a phase-encode gradient magnetic field Ge and a read-out (frequency-encode) gradient magnetic field Gr, respectively, which intersect at right angles with one another. The slice, phase-encode and read-out gradient magnetic fields, Gs, Ge and Gr, are superposed on the static magnetic field B0.

The receiving/transmitting unit includes the RF coil unit 8, the transmitter 9T, and the receiver DR. The RP coil unit 8 is arranged near the subject 200 in the examination space. The transmitter 9T and the receiver 9R are connected to the RE coil unit 8. The transmitter 9T and the receiver 9R operate under the control of the sequencer 10. The transmitter 9T supplies an RF current pulse of Lamor frequency to the RF coil unit 8 in order to induce nuclear magnetic resonance (NMR). The receiver 9R acquires an MR signal (radio-frequency signal), such as an eco signal, which the RF coil unit 8 has received. The receiver 9R then performs, on the MR signal, various processes, such as pre-amplification, intermediate-frequency conversion, phase detecting, low-frequency amplification and filtering. Finally, the receiver 9R performs analog-to-digital (A/D) conversion on the MR signal, producing digital data (raw data).

The control/operating unit includes the sequencer 10, the arithmetic unit 11, the storage unit 12, the display 13, the input device 14, the audio unit 15 and the host computer 16.

The sequencer 10 has a CPU and a memory. The sequencer 10 receives pulse sequence information from the host computer 16. The pulse sequence information is stored into the memory. The CPU of the sequencer 10 controls the gradient power supply 7, transmitter 9T and receiver 9R in accordance with the sequence information stored in the memory. The CPU also receives the raw data output from the receiver DR and transfers the raw data to the arithmetic unit 11. Note that the sequence information is all data necessary for operating the gradient power supply 7, Transmitter 9T and receiver 9R in accordance with the pulse sequence.

The arithmetic unit 11 receives the raw data output from the transmitter 9T, through the sequencer 10. The arithmetic unit 11 has an internal memory. The internal memory has k-space (also known as Fourier space or frequency space), in which the raw data input to the arithmetic unit 11 is stored. The raw data is subjected to two- or three-dimensional Fourier transform, thereby reconstructing video data for the real space. The arithmetic unit 11 can perform, if necessary, synthesis and differential operation (including weighted differentiation) on any data representing an image. The synthesis includes cumulative addition of pixel values, maximum intensity projection (MIP), minimum intensity projection (minIP), and the like. As another example of the synthesis, the axes of several frames may be aligned in a Fourier space, and the raw data items representing these frames may be synthesized, thereby generating one-frame raw data. The addition of pixel values may be simple addition, arithmetic-mean process or weighted-mean process.

In this embodiment, acquisition of a positioning image, a monitoring image, and a diagnostic image in regard to the subject 200 can be performed based on operations of the gradient power supply 7, transmitter 9T, and receiver 9R and processing in the arithmetic unit 11 under control of the sequencer 10 in particular. It should be noted that the positioning image, monitoring image, and diagnostic image will be described later.

The storage unit 12 stores video data reconstructed or video data subjected to the above-mentioned synthesis or differential operation.

The display 13 can display various images to the operator, under the control of the host computer 16. The display 13 is, for example, a display device such as a liquid crystal display.

The input device 14 is operated to input various data items such as parameter information for synchronous timing selection, scanning conditions the operator desires, the pulse sequence, data about the image synthesis and differential operation, and the like. These data items are sent from the input device 14 to the host computer 16. The input device 14 comprises, as the case may be, a pointing device such as a mouse or a track ball, a section device such as a mode-switching panel, or a device such as keyboard.

The audio unit 15 generates messages for the start and end of breath holding as sounds under the control of the host computer 16.

The host computer 16 can perform various functions when a prescribed software routine is executed. One of the functions is to manage the units constituting the MRI apparatus 100 so that the apparatus 100 performs such various operations as the existing MRI apparatus performs. One of these functions is to instruct the pulse sequence information to the sequencer 10 and to control operations of the entire apparatus. One of the functions is to set a region of interest in the positioning image in accordance with specification made by an operator. One of the functions notifies the operator of information that guides a region that is preferable as the region of interest by controlling the display 13 to display an image representing the region preferable as the region of interest when setting the region of interest. One of the functions combines a region-of-interest image showing the region of interest with a monitoring image to generate a display image every time the monitoring image is acquired. One of the functions controls the sequencer 10 in such a manner that repeated acquisition of a monitoring image is started after acquiring a positioning image and acquisition of the monitoring image is stopped in response to an instruction of acquiring a diagnostic image issued by an operator after start of repeated acquisition, thereby imaging the diagnostic image. Further, one of the functions controls the display 13 to display the latest generated display image.

The electrocardiograph unit includes an ECG sensor 17 and an ECG unit 18. The ECG sensor 17 may be attached to the subject 200 to detect an ECG signal from the subject 200. The ECG signal is an electrical signal (hereinafter referred to as a sensor signal). The ECG unit 18 performs various processes, including binary encoding, on the sensor signal.

The sensor signal thus processed is output to the sequencer 10. The electrocardiograph unit is, for example, a vector electrocardiograph. The sequencer 10 uses the sensor signal generated by the electrocardiograph unit, when it is necessary to carry out a scan in synchronism with the cardiac phase of the subject 200.

An operation of the MRI apparatus 100 having the following structure will now be described.

FIG. 2 is a flowchart showing a processing produce for contrast MRA imaging by the host computer 16.

In step Sa1, the host computer 16 instructs the sequencer 10 and the arithmetic unit 11 to acquire a positioning image. The positioning image can be obtained with a range and a resolution that enable identifying a position of a target region which is a target of the contrast MRI imaging or a peripheral region thereof. However, the positioning image does not require a resolution close to that of a diagnostic image used for diagnosis. Thus, for acquisition of the positioning image, a technique enabling imaging in a short time, for example, a steady-state free precession (SSFP) method or a high-speed spin echo method which also uses an inversion pulse, is preferred. It should be noted that the former technique is a white blood imaging method enabling representing a blood vessel with a high luminance and the latter technique is a black blood imaging method enabling representing a blood vessel with a low luminance. The positioning image may be acquired for setting of a later-described judgment region alone, or the positioning image utilized to set an imaging range of main imaging may be used to set the later-described judgment region.

In step Sa2, the host computer 16 generates a judgment region setting image and displays this image by the display 13. FIG. 3 is a view showing an example of a judgment region setting image 300. The judgment region setting image 300 includes a positioning image 301 and guide images 302 and 303. The positioning image 301 is an image obtained in step Sa1. The guide image 302 is an image prepared to display a setting example of the Judgment region. The guide image 303 is an image prepared to display a name of a region that should be included in the judgment region in the form of characters. For example, when a target region is a pulmonary artery, it is empirically known that starting acquisition of a diagnostic image (which will be referred to as main imaging hereinafter) at a time point that a contrast medium reaches a point where a superior vena cava enters a right atrium is preferred. It is desirable for the judgment region to be set to include an object region which is an object for a judgment on a start timing of main imaging in this manner. Thus, as the guide image 302, an image showing the judgment region set to include, for example, the superior vena cave is prepared in advance. This guide image 302 is presented to an operator as a reference, and hence it may be based on an image or an illustration acquired in regard to a subject different from the subject 200. The guide image 303 is an image representing, for example, the name of an object region in the form of characters. Data of these guide images 302 and 303 is stored in, for example, the storage unit 12. It should be noted that both the guide images 302 and 303 do not have to be necessarily included, and one of these images can suffice. An operator who is skilled in the contrast MRA imaging may not require the guide images 302 and 303, and hence both the images may be omitted. It should be noted that the host computer 16 may determine whether display of each of the guide images 302 and 303 is required in response to a request from the operator in order to adapt to operators having various skills and a necessary guide image alone may be included in the judgment region setting image 300.

Figure 4:
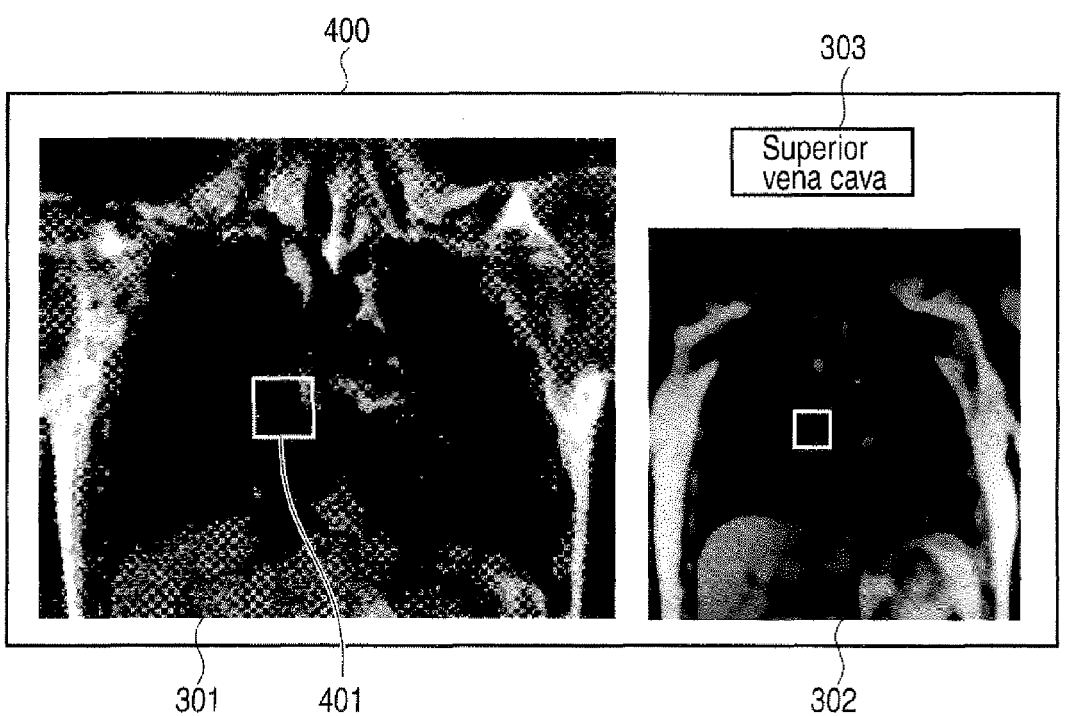
FIG. 4 is a view showing a setting example of a judgment region.

In step Sa3, the host computer 16 sets the judgment region on the positioning image in response to an instruction from the operator. To set the judgment region, a known image ROI setting function that uses a pointing device such as a mouse to draw a polygonal mark, a dot, or a line segment and thereby sets an arbitrary region on an image can be used. FIG. 4 is a view showing a setting example of the judgment region, and depicts an example of a judgment region setting image 400 in which an image 401 representing a judgment region is combined with the positioning image 301.

In step Sa4, the host computer 16 instructs the sequencer 10 and the arithmetic unit 11 to start monitoring imaging. In response to this instruction, the sequencer 1C and the arithmetic unit 11 starts monitoring imaging that repeatedly obtains a monitoring image. The monitoring image must be obtained in a short cycle enabling recognition of a state of movement of the contrast medium (for example, 1 second). Thus, a resolution or the like is set to a low value, thereby obtaining one monitoring image in a short time. For example, a gradient echo type pulse sequence can be utilized for monitoring imaging. That is, monitoring imaging is so-called spectroscopy. Furthermore, it is general to reduce contrast of a region having no contrast medium in the monitoring image in order to emphasize the contrast. Therefore, at least one of a resolution and contrast of the monitoring image is inferior to that of the positioning image.

In a state where monitoring imaging is carried out, the host computer 16 waits until acquisition of one monitoring image is completed or the operator instructs start of main imaging in steps Sa5 and Sa6.

Figure 5:
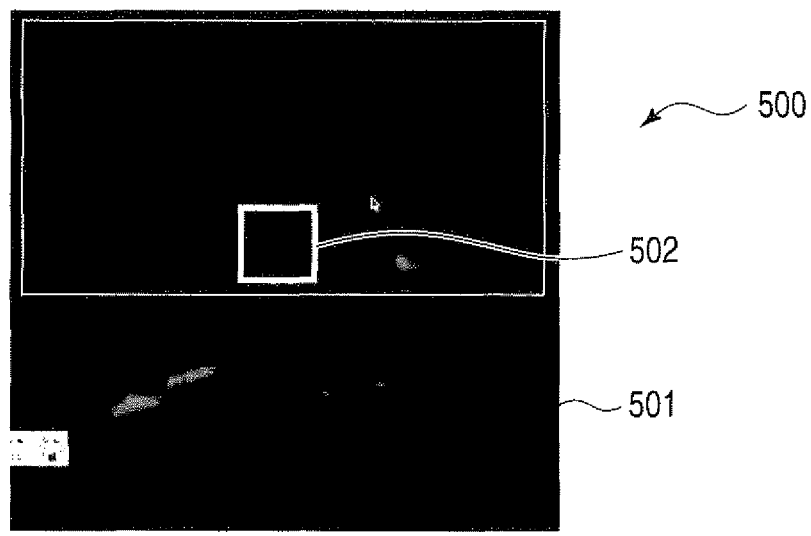
FIG. 5 is a view showing an example of a display image before a contrast medium reaches a judgment region.

When acquisition of one monitoring image is completed, the host computer 16 advances to step Sa6 from step Sa5. In step Sa6, the host computer 16 generates a display image in which a judgment region image representing the judgment region set in step Sa3 is superimposed on the newly acquired monitoring image, and displays this image in the display 13. FIG. 5 is a view showing an example of a display image 500 generated before the contrast medium reaches the judgment region. This display image 500 shows a judgment region image 502 superimposed on a monitoring image 501. Then, the host computer 16 returns to the standby mode of steps Sa5 and Sa6. In this manner, the display image in which the judgment region image is superimposed on the new monitoring image is generated every time the new monitoring image is obtained until start of main imaging is instructed, and the display image is displayed in the display 13.

It should be noted that an imaging slice of the monitoring image may be the same as or different from an imaging slice of the positioning image. The two different imaging slices may be parallel to each other or may have different directions. When the monitoring image and the positioning image have different slices, a central point of the judgment region set in step Sa3 is determined as the center of a point where monitoring image is subjected to projection, and an image representing a region having the same size and shape is determined as the judgment region image.

Figure 6:
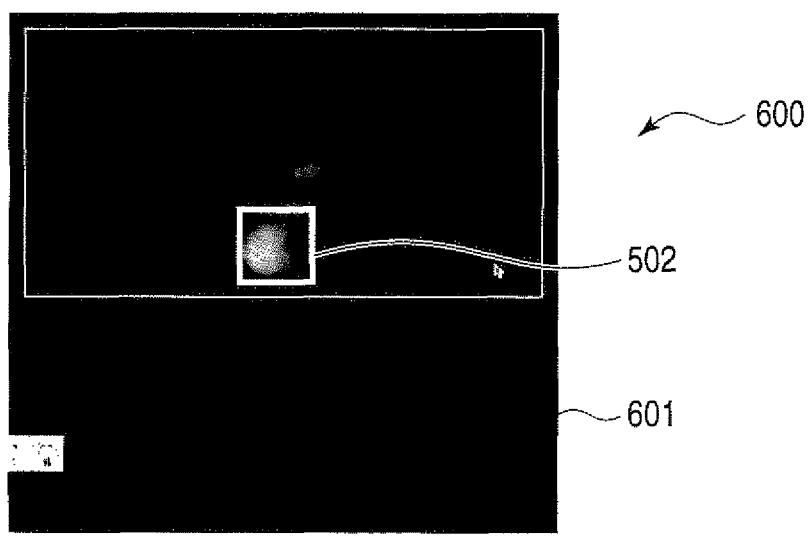
FIG. 6 is a view showing an example of a display image in a state where the contrast medium has reached the judgment region.

In the display image, the judgment region set in step Sa3 is continuously displayed as the judgment region image, but the monitoring image is sequentially updated. Therefore, how the contrast medium moves in the imaging region of the monitoring image is shown in the display image. FIG. 6 is a view showing an example of a display image 600 in a state where the contrast medium has reached the imaging region. In this display image 600, the contrast medium shown with a high signal value in the Judgment region represented by the judgment region image 502 is superimposed on a monitoring image 601.

An operator can recognize that the contrast image has reached a target region by viewing this display image 600. Further, based on this recognition, the operator judges the timing for starting main imaging and instructs start of main imaging. Upon receiving this instruction, the host computer 16 advances to a step Sa8 from step Sa6. In step Sa8, the host computer 16 instructs the sequencer 10 and the arithmetic unit 11 to terminate monitoring imaging. In accordance with this instruction, the sequencer 10 and the arithmetic unit 11 terminate monitoring imaging. Subsequently, in step Sa9, the host computer 16 controls each unit to perform main imaging of contrast MRA. An operation of each unit for main imaging may be a known operation. Furthermore, when main imaging is finished, the host computer 16 terminates this processing.

As explained above, according to this embodiment, even though the operator cannot ascertain the position of an object region from the monitoring image, he/she can easily ascertain that the contrast medium has reached the object region, thereby instructing start of main imaging at an appropriate timing.

This embodiment can be modified in many ways as follows.

When setting a judgment region, a positioning image alone may be displayed.

A display image may be displayed by using a display device externally provided to the MRI apparatus 100.

Notification of guidance information is not restricted to display of a guidance image, and it may be carried out in a different conformation, for example, output of a sound message.

The present invention can be applied to MRA imaging using no contrast medium or imaging targeting a fluid other than blood. As the MRA imaging using no contrast medium, there is known a method of making the same contrast change as that of the contrast image by labeling blood or the like, for example, an arterial spin labeling method. Alternatively, there is known a method of changing an initial value of a signal intensity by using a magnetization transfer contrast (MTC) pulse or an inversion pulse to observe a change with time.

A monitoring image may be generated as a difference image between an image obtained by the latest single monitoring imaging and an image acquired in the past.

The present invention can be applied to other types of medical imaging apparatuses, for example, an X-ray CT scanner as in the foregoing embodiment.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A medical imaging apparatus comprising:
   a collection unit configured to collect a magnetic resonance signal from a subject by applying a uniform static magnetic field to the subject and also apply a radio-frequency magnetic field and a gradient magnetic field to the subject in accordance with a predetermined pulse sequence;
   a reconstruction unit configured to reconstruct a medical image concerning the subject based on the magnetic resonance signal collected by the collection unit;

a first control unit configured to control the collection unit and the reconstruction unit to acquire the medical image as a positioning image that is used to set a position of a judgment region, the judgment region being a region on monitoring images for a judgment on start timing of main imaging;

a notification unit configured to notify the operator of guidance information that is used to guide a region preferable as the judgment region;

a setting unit configured to set the judgment region in the positioning image in accordance with specification performed by an operator;

a second control unit configured to control the collection unit and the reconstruction unit providing control so as to repeatedly acquire the medical image as a monitoring image;

wherein; the second control unit configured to, when the monitoring image is repeatedly acquired, control the collection unit and the reconstruction unit providing control to stop acquisition of the monitoring image and acquire the medical image as a diagnostic image; and a third control unit configured to control a display to display the monitoring images repeatedly acquired by the collection unit and the reconstruction unit and to display judgment region image representing the judgment region set by the setting unit in the monitoring image identifiably combine with the monitoring images;

wherein the notification unit is configured to control the display to display an image prepared to display a setting example of the judgment region as the guidance information.

2. The medical imaging apparatus according to claim 1, wherein:
the acquisition of the monitoring image is stopped and the medical image as the diagnostic image is acquired, in accordance with instruction of acquisition of the diagnostic image issued by the operator.

3. The medical imaging apparatus according to claim 1, wherein the guidance information is at least one of an image obtained by combining an image similar to the positioning image with an image representing a region preferable as the judgment region in the image and an image showing a part of the subject which should be included in the judgment region in the form of characters.

4. The medical imaging apparatus according to claim 3, wherein the image similar to the positioning image is an image acquired in regard to another subject that is different from the subject.

5. The medical imaging apparatus according to claim 1, wherein at least one of a resolution and contrast of the monitoring image is lower than that of the positioning image.

6. The medical imaging apparatus according to claim 1, wherein the notification unit is configured to control the display to display the guidance information with the positioning image.

7. The medical imaging apparatus according to claim 1, wherein the monitoring image is obtained by contrast magnetic resonance (MR) imaging.

8. A method of generating an image for display in a medical imaging apparatus, the method comprising:
collecting, via a collection unit, a magnetic resonance signal from a subject by applying a uniform static magnetic field to the subject and also applying a radio-frequency magnetic field and a gradient magnetic field to the subject in accordance with a predetermined pulse sequence;

reconstructing, via a reconstruction unit, a medical image concerning the subject based on the magnetic resonance signal collected by the collection unit; and performing, using a computer, steps including:
controlling the collection unit and the reconstruction unit to acquire the medical image as a positioning image that is used to set a position of a judgment region, the judgment region being a region on monitoring images for a judgment on start timing of main imaging;

notifying the operator of guidance information that is used to guide a region preferable as the judgment region;

setting the judgment region in the positioning image in accordance with specification made by an operator;

controlling the collection unit and the reconstruction unit to repeatedly acquire the medical image as a monitoring image;

wherein; the second control unit configured to, when the monitoring image is repeatedly acquired, control the collection unit and the reconstruction unit providing control to stop acquisition of the monitoring image and acquire the medical image as a diagnostic image; and controlling a display to display the repeatedly acquired monitoring images and displaying a judgment region image showing the judgment region set by said setting in the monitoring image identifiably combine with the monitoring images;

wherein the display is controlled to display an image prepared to display a setting example of the judgment region as the guidance information;

wherein: when the monitoring image is repeatedly acquired, the collection unit and the reconstruction unit are controlled to stop acquisition of the monitoring image and acquire the medical image as a diagnostic image.

9. The method according to claim 8, wherein the monitoring image is obtained by contrast magnetic resonance (MR) imaging.

10. A medical imaging apparatus comprising:
a receiver configured to receive a magnetic resonance signal from a subject by applying a uniform static magnetic field to the subject and also apply a radio-frequency magnetic field and a gradient magnetic field to the subject in accordance with a predetermined pulse sequence;

a controller, including a computer, the controller configured to:

reconstruct a medical image concerning the subject based on the received magnetic resonance signal;

provide a first control to acquire the medical image as a positioning image that is used to set a position of a judgment region, the judgment region being a region on monitoring images for a judgment on start timing of main imaging;

notify the operator of guidance information that is used to guide a region preferable as the judgment region;

set the judgment region in the positioning image in accordance with specification performed by an operator;

provide a second control so as to repeatedly acquire the medical image as a monitoring image;

wherein the controller is further configured to, when the monitoring image is repeatedly acquired, stop acquisition of the monitoring image and acquire the medical image as a diagnostic image; and provide a third control to control a display to display the repeatedly acquired monitoring images and display a judgment region image representing the judgment region set by the setting in the monitoring image identifiably combine with the monitoring images;

wherein the display is controlled to display an image prepared to display a setting example of the judgment region as the guidance information.

11. The medical imaging apparatus according to claim 10, wherein the acquisition of the monitoring image is stopped and the medical image as the diagnostic image is acquired, in accordance with instruction of acquisition of the diagnostic image issued by the operator.

12. The medical imaging apparatus according to claim 10, wherein the guidance information is at least one of an image obtained by combining an image similar to the positioning image with an image representing a region preferable as the judgment region in the image and an image showing a region part of the subject which should be included in the judgment region in the form of characters.

13. The medical imaging apparatus according to claim 10, wherein the contrast of a region having no contrast medium in the monitoring image is reduced so that a resolution of the monitoring image is lower than that of the positioning image.

14. The medical imaging apparatus according to claim 10, wherein the contrast of a region having no contrast medium in the monitoring image is reduced so that the contrast of the monitoring image is lower than that of the positioning image.

15. The medical imaging apparatus according to claim 10, wherein the monitoring image is obtained by contrast magnetic resonance (MR) imaging.

16. The medical imaging apparatus according to claim 12, wherein the image similar to the positioning image is an image acquired in regard to another subject that is different from the subject.

17. The medical imaging apparatus according to claim 10, wherein the controller is further configured to control the display to display the guidance information with the positioning image.

* * * * *